(12) United States Patent
Pagnanelli et al.

(10) Patent No.: US 10,335,057 B2
(45) Date of Patent: Jul. 2, 2019

(54) METHOD AND APPARATUS FOR DEPTH MEASUREMENT

(71) Applicants: Christopher Pagnanelli, Huntington Beach, CA (US); James F Bauer, Lake Forest, CA (US)

(72) Inventors: Christopher Pagnanelli, Huntington Beach, CA (US); James F Bauer, Lake Forest, CA (US)

(73) Assignee: Exaxion Scientific, LLC, Mission Viejo, CA (US)

( * ) Notice: Subject to any disclaimer, the term of this patent is extended or adjusted under 35 U.S.C. 154(b) by 152 days.

(21) Appl. No.: 15/679,236

(22) Filed: Aug. 17, 2017

(65) Prior Publication Data

US 2018/0049673 A1     Feb. 22, 2018

Related U.S. Application Data

(60) Provisional application No. 62/377,027, filed on Aug. 19, 2016.

(51) Int. Cl.
| | |
|---|---|
| *A61B 5/107* | (2006.01) |
| *A61B 90/00* | (2016.01) |
| *A61B 5/00* | (2006.01) |
| *G01B 3/28* | (2006.01) |
| *A61B 34/20* | (2016.01) |

(52) U.S. Cl.
CPC .......... *A61B 5/1076* (2013.01); *A61B 5/4504* (2013.01); *A61B 90/06* (2016.02); *G01B 3/28* (2013.01); *A61B 2034/2051* (2016.02); *A61B 2034/2063* (2016.02); *A61B 2090/061* (2016.02); *A61B 2090/062* (2016.02)

(58) Field of Classification Search
CPC .................................................... A61B 5/1076
USPC ............................................................ 33/512
See application file for complete search history.

(56) References Cited

U.S. PATENT DOCUMENTS

| | | | | |
|---|---|---|---|---|
| 4,033,043 A * | 7/1977 | Cunningham | ....... | A61B 5/1076 33/542 |
| 7,165,336 B2 * | 1/2007 | Kim | ..................... | A61B 5/1076 33/512 |
| 7,493,703 B2 | 2/2009 | Kim et al. | | |
| 7,676,943 B2 | 3/2010 | Kim et al. | | |
| D616,095 S * | 5/2010 | Kim | ..................... | A61B 5/1076 D24/133 |
| 7,730,629 B2 | 6/2010 | Kim | | |
| D634,843 S * | 3/2011 | Kim | ..................... | A61B 5/1076 D24/133 |
| 9,918,796 B2 * | 3/2018 | Kortenbach | ........... | A61B 90/06 |
| 10,132,607 B2 * | 11/2018 | Rioux | .................... | A61B 17/17 |
| 2006/0041241 A1 * | 2/2006 | Herndon | ................ | A61B 5/053 604/500 |
| 2008/0104855 A1 * | 5/2008 | Kim | ........................ | G01B 3/28 33/836 |

* cited by examiner

*Primary Examiner* — George B Bennett
(74) *Attorney, Agent, or Firm* — Joseph G. Swan, P.C.

(57) ABSTRACT

Provided are, among other things, systems, apparatuses methods and techniques for performing a semi-autonomous and/or autonomous measurement of the depth of a hole drilled into bone during a medical/surgical procedure. One such apparatus is activated by a tactile command, provides a digital readout of hole depth, and includes a controller module, a stepper/encoder unit, a linear actuator, and a position sensor.

14 Claims, 9 Drawing Sheets

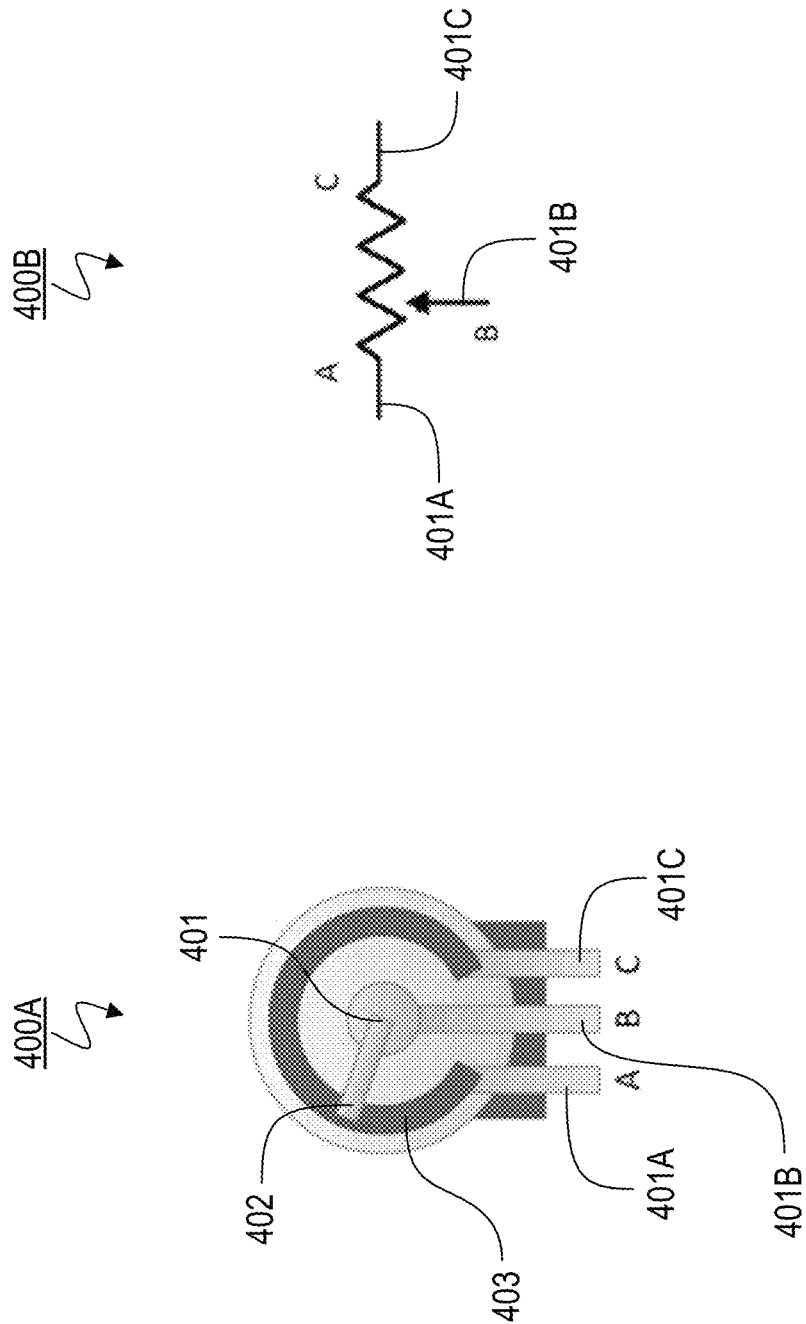

METHOD AND APPARATUS FOR DEPTH MEASUREMENT

FIELD OF THE INVENTION

The present invention pertains, among other things, to systems, apparatuses, methods and techniques for measuring the depth of a hole drilled into a bone, thereby permitting determination of the appropriate lengths for the surgical screws and fasteners used in repairing fractured bones during medical/surgical procedures.

BACKGROUND

To facilitate the healing process, modern medical/surgical procedures which include certain orthopedic, plastic, and podiatric operations, often utilize pins and/or screws to positionally fix (or maintain) bones that are broken or fractured. The repair of serious fractures involves arranging and temporarily fixating the fragmented pieces of bone, drilling a hole completely or partially through the broken bones, and inserting a pin or screw into the drilled holes to secure the pieces together. The pins, screws, and/or any fasteners must be of precise length in order to hold the fragments of bone together in a proper state of fixation. If the length is too short, the reduction of the fracture is weak or unstable. Conversely, if the length is too long, the fastener protrudes from the bone into the surrounding tissue, and can damage vital anatomic structures, such as arteries, veins and/or nerves. The depth of drilled holes varies because each bone in the body is unique in shape, size, and thickness. Consequently, surgeons find it necessary and imperative to precisely measure the depth of the completely drilled holes (through holes) or partially drilled holes (blind holes), so that a fastener of correct length can be selected to complete the surgical repair.

The conventional instruments that surgeons use to measure the depth of holes drilled into bone include mechanical gauges that employ various hooks and/or expanding physical elements on one end of a calibrated rod. Mechanical depth gauges typically comprise a central probe member having a barb at the distal (far) end, and a reciprocating sleeve that encircles the proximal (near) end of the central probe member. Conventionally, the central probe member is slidably connected to the reciprocating sleeve, such that central probe member slides freely back and forth to facilitate manual operation and measurement. To measure the depth of a hole in a bone, the surgeon abuts the sleeve against the proximal side of the hole, and manually extends the probe member into the hole. After extending the probe member beyond the distal side of the hole, the surgeon retracts the probe member, attempting to find purchase against the distal side of the hole with the barb. Typically, a marker is secured to the central probe member, and the reciprocating sleeve has a graduated linear scale or display unit along a portion of its length that is read visually (e.g., a mechanical ruler) or electronically (e.g., a linear encoder). The surgeon reads the measurement of depth by examining the position along the graduated scale indicated by the marker, or by reading a display unit attached to the reciprocating sleeve.

Improvements in the conventional analog depth gauge provide for more readable displays (e.g., LCD displays and HOLD buttons, as disclosed in U.S. Pat. No. 7,730,629), and probe tips that include electronic sensors such as optical transducers, inductive loops, etc. (e.g., see U.S. Pat. No. 7,493,703 and U.S. Pat. No. 7,676,943). But even with these improvements, fundamental difficulties persist. Measurement of depth using a conventional depth gauge typically requires significant interaction and difficulty on the part of the surgeon to: 1) manually manipulate a calibrated rod and/or a reciprocating sleeve that encircles a central probe member; 2) precisely locate a bone edge using a barbed hook or time-varying electronic signal from an electronic sensor in the probe tip; and/or 3) make a close examination of a graduated scale. In surgical procedures that require many depth measurements, these difficulties are multiplied.

Conventional methods for measuring the depth/length of a hole that is completely or partially drilled into bone involve tedious mechanical measurements which are made by manual means, and therefore, are subject to potential inaccuracies as a result of human and other errors. There are many complications and costs associated with measurement inaccuracies and placement of incorrect fixation devices into the hole of a bone. Failure to accurately measure the hole in a bone can lead to: 1) a dramatic increase in operating time; 2) increased radiation (X-ray) exposure to the surgeon and/or patient; and/or 3) increased operating costs to the patient and hospital (e.g., due to extended use of facilities, wasting of expensive medical/surgical hardware, higher billable/overtime hours for hospital staff, etc.).

SUMMARY OF THE INVENTION

In order to address the foregoing problems, the present invention utilizes, among other things, certain semi-automated and/or fully automated techniques to improve the speed, accuracy, and safety of measurements of the depth of a hole drilled into a bone. As indicated above, determining when a mechanical depth gauge has purchased/detected the distal boundary (cortex) of a drilled bone is one of the most tedious tasks that a doctor must perform during a medical procedure that involves the fixation of bone. The present invention provides for improved depth measurement apparatuses and methods, which according the various embodiments of the invention, can provide one or more significant benefits, including: 1) reductions in surgical costs by eliminating the wasting of screws/fasteners that are placed into the body, then found to be inappropriate length; 2) reductions in operating times by increasing the speed and accuracy with which the depth of a drilled hole is determined; 3) reductions in radiation exposure to both patient and medical staff by reducing the amount of intraoperative X-rays required during a procedure; 4) improvements in safety by reducing the amount of time a patient is under anesthesia; and 5) reductions in the risk of screw/fastener placement complications to nearby joints, arteries, veins, nerves, ligaments, tendons, and muscles.

Thus, one embodiment of the invention is directed to an apparatus for measuring the depth of a completely or partially drilled hole, which includes: 1) a controller module having a first and second input, and also having a first and second output, and which executes a process for semi-autonomous or autonomous measurements of linear displacement; 2) a switch module having an output that is coupled to the first input of the controller module, and which provides, e.g., through one or more tactile elements (such as a pushbutton or touch sensor), a command interface between the controller module and a human operator; 3) a stepper/encoder unit having an input coupled to the first output of the controller module, and also having an output, and which converts commands from the controller module into discrete amounts of angular or linear mechanical movement; 4) a linear actuator driven by the stepper/encoder unit, and also having a segment which can be inserted into the drilled hole; 5) a position sensor mechanically coupled to the linear actuator, and also having an output, and which produces an electronic signal having a transition in magnitude or intensity that occurs at the distal boundary of a drilled bone surface; and 6) a display unit which is coupled to the second output of the controller module, and which provides a readout indicating a measure of the linear displacement of the linear actuator. In certain embodiments, the steeper/encoder unit is a motorized function comprising a driver, a stepper motor, and a gear mechanism that converts the angular/rotary motion of an axle into the linear motion of a shaft. In certain other embodiments, the stepper/encoder unit includes a slip gear and associated slip detector, that engages when a physical impediment (e.g., partially drilled bone surface) causes a stepper command to produce no incremental angular movement in an axle of the stepper, and/or no incremental linear movement in the shaft of the actuator. The linear actuator slides back and forth in response to the angular or mechanical movements of the stepper/encoder unit, such that the longitudinal position of the actuator is directly proportional to the angular (rotational) position of an axle in the stepper/encoder unit. Preferably, the position sensor is coupled mechanically to the tip of the linear actuator, and incorporates an electronic transceiver which first generates a physical signal (e.g., an audio, ultrasonic or electromagnetic signal or wave) and then receives a reflection or echo of such signal and converts the received signal into an electrical signal, which subsequently is converted into digital values via an analog-to-digital (A/D) converter. In response to one or more commands received from the switch module, the controller module adjusts the position of the linear actuator until transitions in the magnitude or intensity of the signal received from the sensor module indicate the end (boundary) of the drilled hole has been reached and/or until another condition (e.g., obstruction encountered) has been satisfied.

The foregoing summary is intended merely to provide a brief description of certain aspects of the invention. A more complete understanding of the invention can be obtained by referring to the claims and the following detailed description of the preferred embodiments in connection with the accompanying figures.

BRIEF DESCRIPTION OF THE DRAWINGS

In the following disclosure, the invention is described with reference to the attached drawings. However, it should be understood that the drawings merely depict certain representative and/or exemplary embodiments and features of the present invention and are not intended to limit the scope of the invention in any manner. The following is a brief description of each of the attached drawings.

FIG. 5A is a perspective view of a conventional potentiometer which converts the rotary movement of a wiper into a variable resistance, and according a representative embodiment of the present invention, can provide a means of slip detection and/or rotary encoding; and FIG. 5B is an electronic diagram of a conventional potentiometer which illustrates the relationship between wiper movement and variable resistance.

DESCRIPTION OF THE PREFERRED EMBODIMENT(S)

Figure 1:
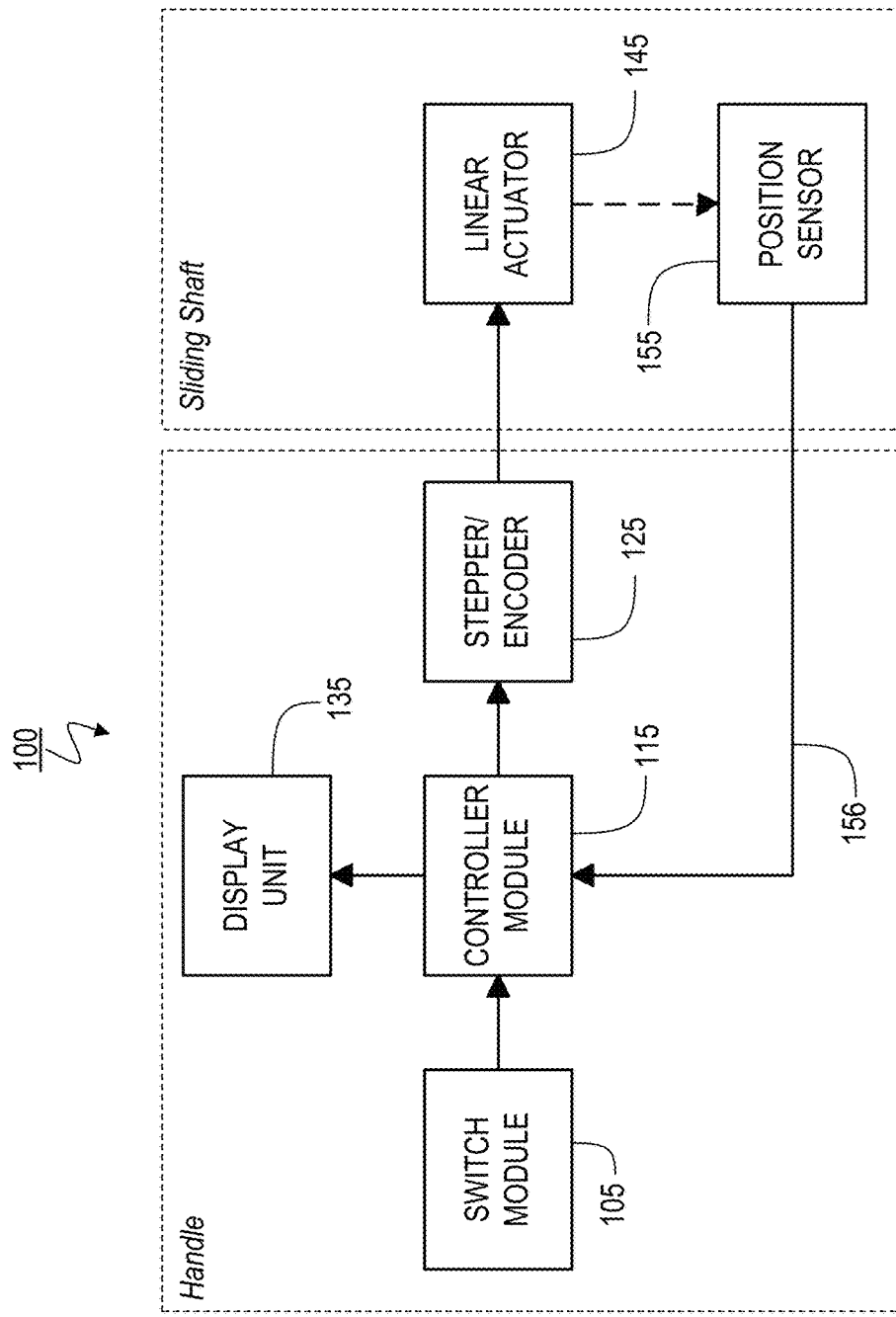
FIG. 1 is simplified block diagram illustrating components of an exemplary bone-depth measurement apparatus, which according to a representative embodiment of the present invention, is capable of autonomous measurements using a controller module in conjunction with a stepper/encoder, a linear actuator, and a position sensor.

A bone-depth measurement assembly which is capable of semi-autonomous and/or autonomous measurement, while providing both greater accuracy and ease of use, is illustrated by the generalized block diagram of FIG. 1. In the preferred embodiments of assembly 100, a handle (primary) element (e.g., element 151, shown in FIG. 2) houses each of switch module 105, controller module 115, stepper/encoder 125, and display unit 135. Linear actuator 145 and position sensor 155 preferably take the form of a cylindrical shaft (secondary) element (e.g., element 145B, shown in FIG. 2), which partly is housed within the handle element 151 and partly protrudes from the handle element, moving back and forth from a more-retracted position in which more of it is disposed within the handle element 151 and a more-extended position in which more of it protrudes from the handle element 151 during normal operation (as discussed in greater detail below), with the protruding portion being capable of being inserted into a drilled hole.

During a medical procedure where a hole has been drilled into a fractured bone, a bone-depth measurement preferably begins with a surgeon grasping the handle element 151 and inserting the tip of linear actuator 145 into the near (proximal) end of the drilled hole. A measurement is initiated by activating controller module 115 with a tactile command to switch module 105 (e.g., depressing a pushbutton or contacting a touch sensor which serves as switch module 105 in a representative embodiment). In response, controller module 115 causes stepper/encoder 125 to drive the tip of linear actuator 145 (or some other point on linear actuator 145, preferably close to its tip) to a point of alignment with the far (distal) end of the drilled hole, based on a signal 156 the controller module 115 receives from position sensor 155 (as discussed in greater detail below).

Preferably, linear actuator 145 is power-driven with a motorized mechanism, but in alternate embodiments, actuator 145 is hand-driven using a (e.g., conventional) ratcheting mechanism. In the preferred embodiments, position sensor 155 is located (mechanically positioned) at or near the very tip of linear actuator 145. Preferably, position sensor 155 uses transmission and reception of sonic or ultrasonic waves such that the received signal includes a transition in magnitude or intensity that indicates alignment with the distal end of the drilled bone (i.e., the distal boundary of the hole). More preferably, position sensor 155 transmits an ultrasonic signal (e.g., as a continuous signal or as a sequence of pulses) and measures the intensity of the reflected echo (e.g., using a directional receiver) from bodily tissues, such as bone and other softer tissues. In alternate embodiments, however, position sensor 155 continuously transmits, and then receives reflections of, electromagnetic waves, e.g., at radio, infrared or light frequencies. Since hard bone (e.g., the outer portion of the bone, as opposed to the interior marrow) is known to produce a larger echo than other tissues, the sensor 155 can be configured such that the reflected echo is at a maximum when aligned with hard bone, and the magnitude of the reflected echo quickly transitions from this relatively higher value to a relatively lower value (i.e., steps) at the boundary between hard bone and other tissue (i.e., transitions in the intensity of reflected echo occur at the end of a drilled hole where there is a corresponding transition from hard bone to other tissue). Detection of the distal boundary of the drilled hole preferably is enhanced with the use of multiple receiver elements which are (e.g., uniformly) arranged at or near the tip of linear actuator 145. However, in alternate embodiments a single receiver element is utilized. Also, in still further embodiments, a single element is used for both transmission and reception (e.g., by transmitting one or more pulses and then receiving the echo or other type of reflected signal following such transmission). At the point of sensor alignment with the distal boundary (i.e., sharp drop-off in the received signal), the depth of the drilled hole is determined by a process implemented within controller module 115, which preferably multiplies the number of step commands provided to stepper/encoder 125, by the linear distance traversed with each step, and potentially by adding or subtracting a constant (e.g., determined through a calibration procedure). The depth of linear actuator 145 is then provided in metric or standard units, to display unit 135 which uses audible tone, or other such alarm, to alert the operator of a completed measurement.

Figure 2:
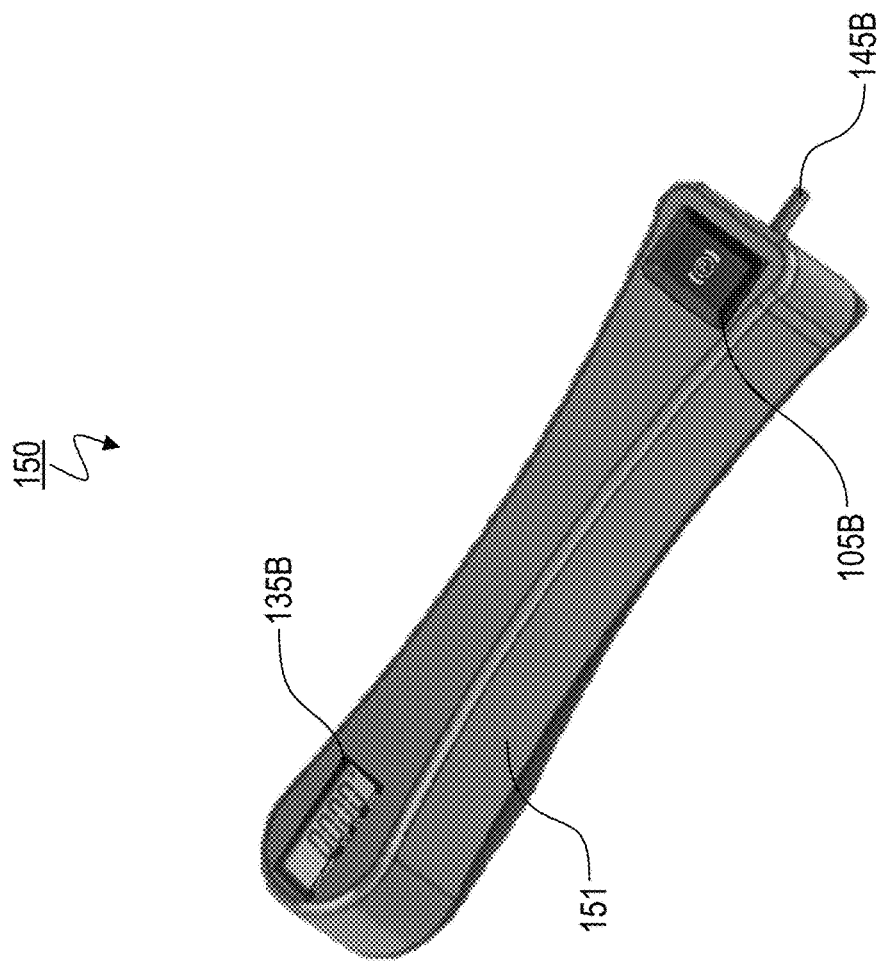
FIG. 2 is a perspective view of an exemplary bone-depth measurement apparatus, according to a representative embodiment of the present invention, which includes a handle assembly with integrated liquid-crystal display and control switch.

A representative mechanical construction for a bone-depth measurement apparatus 130, according to certain preferred embodiments of the invention, is shown in FIG. 2. Preferably the handle (or main housing) 151 has a form factor which is comfortably held within the palm of a single hand (e.g., elongated and not more than 1.5-2.5 inches wide), while providing access to activation switch 105B via a thumb or finger on the same hand (i.e., with the apparatus preferably configured for one-handed operation). In the preferred embodiments, linear actuator 145B moves back and forth within main housing 151 (i.e., actuator 145B adjustably extends and retracts from within housing 151) and is a shaft (rack) having a circular cross-section with a diameter that is less than or equal to the diameter of the hole intended to be drilled completely (i.e., a through hole) or drilled partially (i.e., a blind hole) into the fractured bone. Linear actuators of different lengths and diameters may be used in various embodiments of the measurement apparatus 130.

Display unit 135B preferably is integrated into main housing 151, at a location and orientation that provides for clear visibility while being held in the hand of the operator. In alternate embodiments, however, the display value is held for a period of time, such that the display unit may be visible only after the main housing is removed from the hand of the operator (or the apparatus otherwise is no longer being actively operated). In addition to display unit 135B and activation switch 105B, main housing 151 contains the controller module (e.g., controller module 115) and stepper/encoder module (e.g., stepper/encoder 125) shown in FIG. 1, in addition to a power source for the entire measurement apparatus. In the preferred embodiments, the measurement apparatus is powered by an internal battery and, if appropriate, a voltage converter, which are integrated into (or otherwise disposed within) main housing 151. In alternate embodiments, however, the power source is external, and the main housing includes only the power converter (if appropriate and not included within the external power source) and an associated electrical plug.

Figure 3:
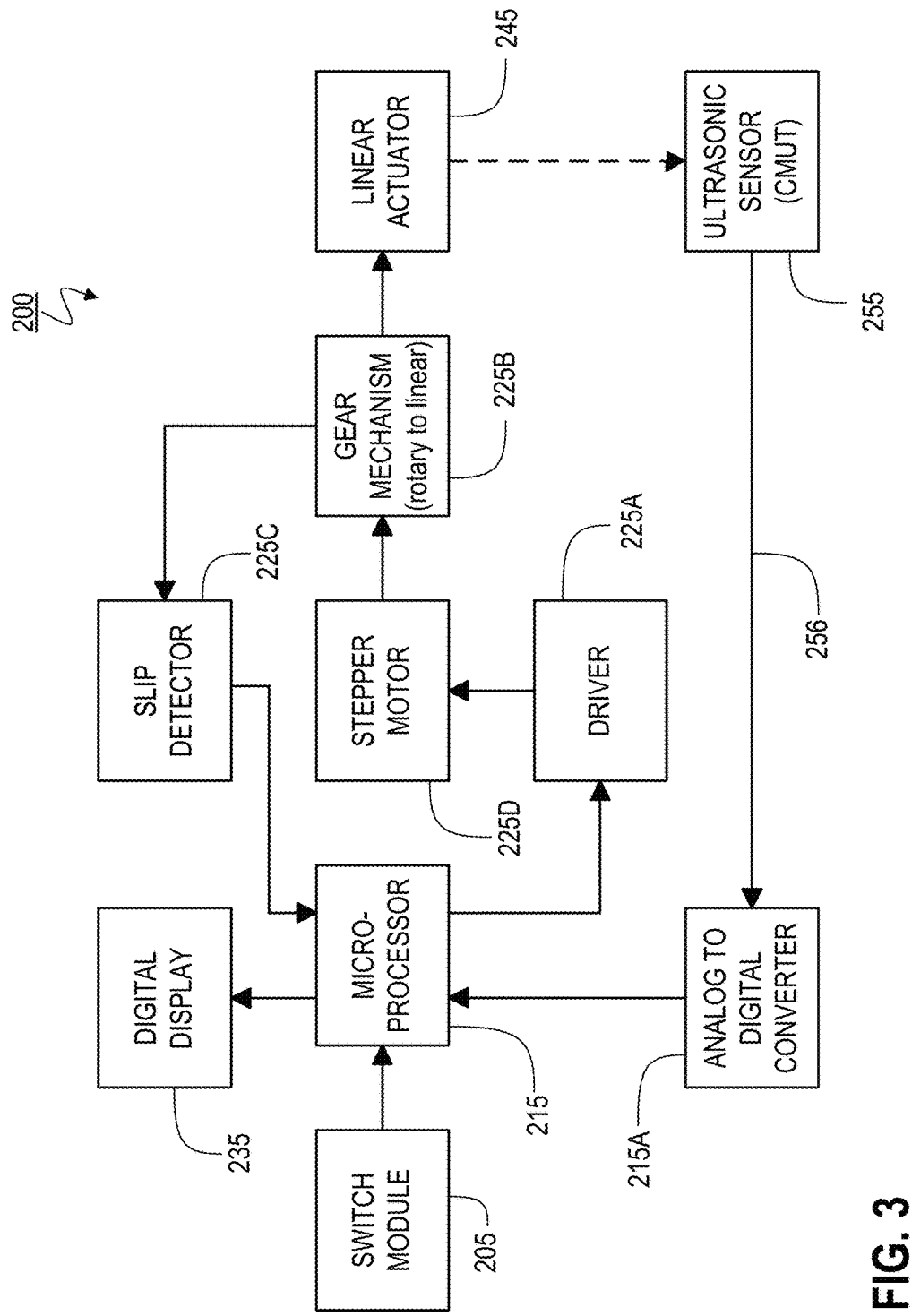
FIG. 3 is a simplified block diagram illustrating components of an exemplary bone-depth measurement apparatus, which according to a representative embodiment of the present invention, is capable of autonomous measurements using a microcontroller in conjunction with a stepper motor/driver, a gear mechanism, a linear actuator, an ultrasonic position sensor, and an analog-to-digital converter.

FIG. 3 illustrates an exemplary embodiment of a bone-hole-depth measurement assembly 200, which is a more specific example of assembly 100 shown in FIG. 1. In exemplary embodiment 200, the linear displacement of linear actuator 245 (relative to the housing) is adjusted via stepper motor 225D and gear mechanism 225B. Gear mechanism 225B preferably translates discrete rotary (angular) steps in the axle of stepper motor 225D, into linear motion via a linkage that engages threads or grooves that are machined into the actuator shaft. Conventionally, such a gear mechanism is sometimes referred to as a rack-and-pinion system. The conversion from rotary motion to linear motion is according to a constant that depends on the pitch of the threads (or grooves), and the gear ratio associated with gear mechanism 225B. Low-cost, conventional stepper motors have step angles as small as 15-18 degrees (i.e., 20-24 steps per revolution), and accuracies as good as one degree. Gear ratios can be made sufficiently small to produce what is effectively a continuous range of operation, and a resulting torque that is sufficient to drive the actuator shaft into a drilled hole. In alternate embodiments, gear mechanism 225B is replaced by a friction engagement between the rotating element of the stepper motor 225D and the edge of linear actuator 245 (e.g., using one or more high-friction resilience surfaces and maintaining sufficiently high pressure between the two components).

In the preferred embodiments, the linear displacement of actuator 245 is measured as a constant multiplied by the number of steps executed by stepper motor 225D. However, in alternate embodiments, the linear displacement of actuator 245 is measured directly by a conventional linear encoder or other conventional means.

The output of slip detector 225C indicates a condition where, due to an obstruction-induced gear slip, a step command from microprocessor 215 produces no incremental rotary movement in the axle of stepper motor 225D, and therefore, produces no incremental linear displacement in the shaft of actuator 245. Such an obstruction can be caused, for example, by the hard surface at the distal end of a partially drilled bone (e.g., a blind hole that does not pass completely through a bone). The output of the slip detector preferably is monitored to detect the distal end of a partially drilled bone, and therefore, a measurement assembly according to the preferred embodiments has utility in medical procedures where drill holes do not pass completely through a bone (i.e., there is no boundary between bone and tissue at the distal end of the drilled hole).

In the preferred embodiments of assembly 200, an ultrasonic sensor (e.g., sensor 255) is utilized to align the tip of (or other known position on) linear actuator 245 with the distal end of a completely drilled bone (i.e., the distal boundary between hard bone and softer tissue based on transitions in the magnitude of the sensor output 256, which is proportional to (or otherwise a function of) intensity of the reflected echo). Preferably, sensor 255 comprises one or more capacitive micromachined ultrasonic transducers (CMUTs), which transmit ultrasonic waves onto hard bone and softer tissue surfaces, and which measure the intensity of ultrasonic echo (reflected) waves from hard bone and softer tissue surfaces. Such devices provide a desired combination of small size, low cost, and reliable performance. In alternate embodiments, however, sensor 255 comprises other types of conventional transducers, such as piezoelectric micromachined ultrasonic transducers (PMUTs), or comprises radio frequency (RF, e.g., capacitors, inductors) or optical components. In the exemplary embodiment of assembly 200, the output 256 of sensor 255 is coupled to microprocessor 215 via an analog-to-digital converter 215A, which transforms a continuous-time and continuously-variable signal at the output of sensor 255, into a representative discrete-time and discretely-variable signal at the input of microprocessor 215.

It should be noted that in the representative embodiment of assembly 200, microprocessor 215 is coupled to linear actuator 245 through an arrangement of distinct components, which include a driver function (e.g., driver 225A), a rotary stepper function (e.g., stepper motor 225D), a rotary-to-linear function (e.g., gear mechanism 225B), and a slip detection function (e.g., detector 225C). Those skilled in the art will readily appreciate that the functions of driving, stepping, gearing, and detecting can be integrated into single component, and such integrated embodiments should be considered within the scope of the invention. Furthermore, in the representative embodiment of assembly 200, microprocessor 215 and analog-to-digital converter 215A are shown as distinct elements. It is common, however, for conventional microprocessors to include an analog-to-digital conversion function, and alternate embodiments where the analog-to-digital conversion function is performed within the microprocessor also should be considered within the scope of the invention. More generally, any of the distinct functions that comprise the representative embodiment of assembly 200 may be integrated with any other function in any manner, and such alternate embodiments should be considered within the scope of the invention.

In the preferred embodiments of the invention, the rotary motion of a stepper/encoder is converted to linear motion using a gear mechanism (e.g., the rotary motion of stepper motor 225 is converter to the linear motion of actuator 245 via gear mechanism 225B). Preferably, the stepper function is provided directly by a stepper motor. In alternate embodiments, however, the stepper function is provided by a servo system comprising a linear (continuous) motor and an angular position sensor (e.g., a rotary encoder). The preferred gear mechanism depends on the desired mechanical dimensions of the handle (e.g., main housing 151 in FIG. 2), and is derived from conventional methods such as those illustrated in FIGS. 4A-D. Conventional gear mechanism 300A of FIG. 4A, converts the rotary motion about a particular axis into linear motion along a parallel axis through the combination of a worm gear (e.g., threaded gear 301A), a gear wheel (e.g., 8-toothed worm wheel 302A), and a square rack (e.g., toothed rack 303A).

Figure 4B:
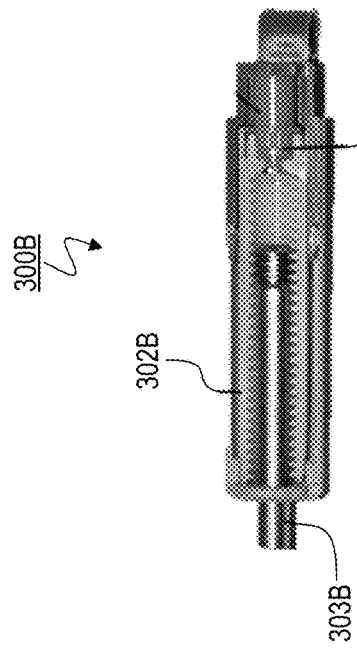
FIG. 4B is a perspective view of an alternate conventional gear mechanism, which is used to convert angular rotation about a particular axis, into linear motion along a parallel axis.
Figure 4D:
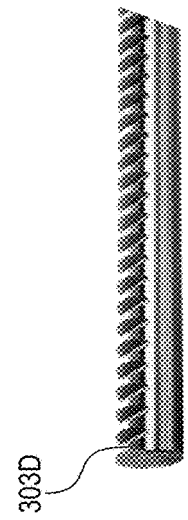
FIG. 4D is a perspective view of a round rack that conventionally is used in rack and pinion mechanisms.
Figure 4A:
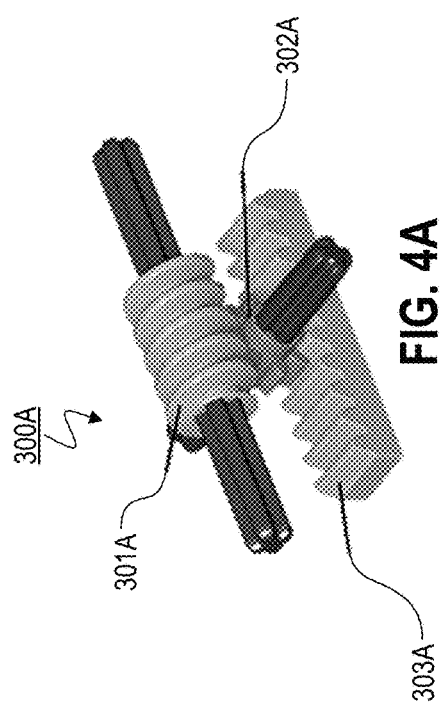
FIG. 4A is a perspective view of a conventional gear mechanism, which is used to convert angular rotation about a particular axis into linear motion along a parallel axis.
Figure 4C:
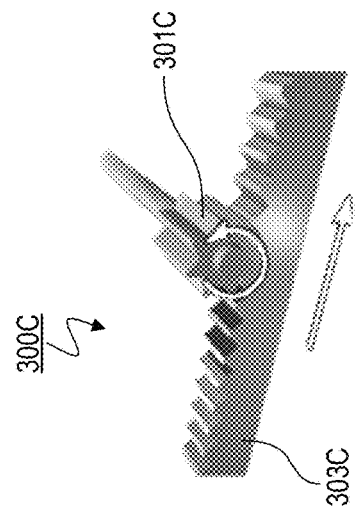
FIG. 4C is a perspective view of a conventional rack and pinion mechanism, which converts angular rotation about a particular axis, into linear motion along a perpendicular axis.

Conventional gear mechanism 300B of FIG. 4B provides an alternate conventional means of converting rotary motion about a particular axis to linear motion along a parallel axis. Gear 300B uses rotating clutch assembly 301B to drive threaded tube 302B, which in turn pushes threaded piston 303B (i.e., the rotary motion of the clutch assembly is converted to the linear motion of the threaded piston). Gear mechanism 300C of FIG. 4C, conventionally is referred to as a rack and pinion system, where the rotation of pinion 301C about a particular axis, is converted to the linear motion of square rack 303C along a perpendicular axis. Conventional gear mechanisms 300A&C utilize square racks (e.g., rack 303A of gear 300A and rack 303C of gear 300C). In the preferred embodiments, the rack is cylindrical (e.g., conventional round rack 303C of FIG. 4D) in order to conform to and pass more easily through a drilled hole.

In the preferred embodiments of the invention, the linear displacement of an actuator (e.g., actuator 245 of assembly 200) is determined by step commands which effect an angular displacement in the axle of a stepper motor (e.g., stepper motor 225 of assembly 200), and a slip detector indicates when a step command produces no incremental angular displacement in the motor and/or no linear displacement in the actuator. In alternate embodiments, the linear displacement of an actuator is determined by step commands to a servo mechanism comprising a linear (continuous) motor and a rotary encoder. Conventional potentiometer 400A, shown in FIG. 5A, can provide a means of slip detection and/or rotary encoding in the various embodiments of the invention. Potentiometer 400A converts the angular displacement of wiper 402 into a corresponding resistance across electrical terminals 401A&B. As wiper 402 rotates in a clockwise direction on axle 401, it makes electrical contact with resistive material 403 at a point which is progressively further in distance from terminal 401A (i.e., a point which is progressively further along the circular path of resistive material 403). The total resistance between terminals 401A&B therefore increases in direct proportion with this distance because at further distances, a signal incident on terminal 401A much traverse a greater length of resistive material to arrive at terminal 401B. In embodiments where slip detection includes a conventional potentiometer, axle 401 preferably is coupled to the axle of the stepper motor (or linear motor), such that a change in resistance across terminals 401A&B provides both an indication of angular displacement in the axle of the stepper motor, and an indication of a corresponding linear displacement in the shaft of the associated actuator. Conversely, a step command that produces no angular displacement in the axle of the stepper motor, and/or no corresponding linear displacement in the shaft of the actuator, is indicated by no change in resistance across terminals 401A&B. In a similar fashion, angular movement in the axle of a linear motor can be encoded (i.e., quantized) by coupling the axle of the motor to axle 401 of potentiometer 400A, and detecting the resistance across terminals 401A&B of the potentiometer. In should be noted that exemplary potentiometer 400A employs a single-turn mechanism (i.e., minimum and maximum resistance at terminals 401A&B are realized over 360 degrees of angular displacement), but instead, conventional multi-turn potentiometers may be utilized to ease the gearing requirements for coupling the axle of the potentiometer to the axle of the motor.

Figure 6A:
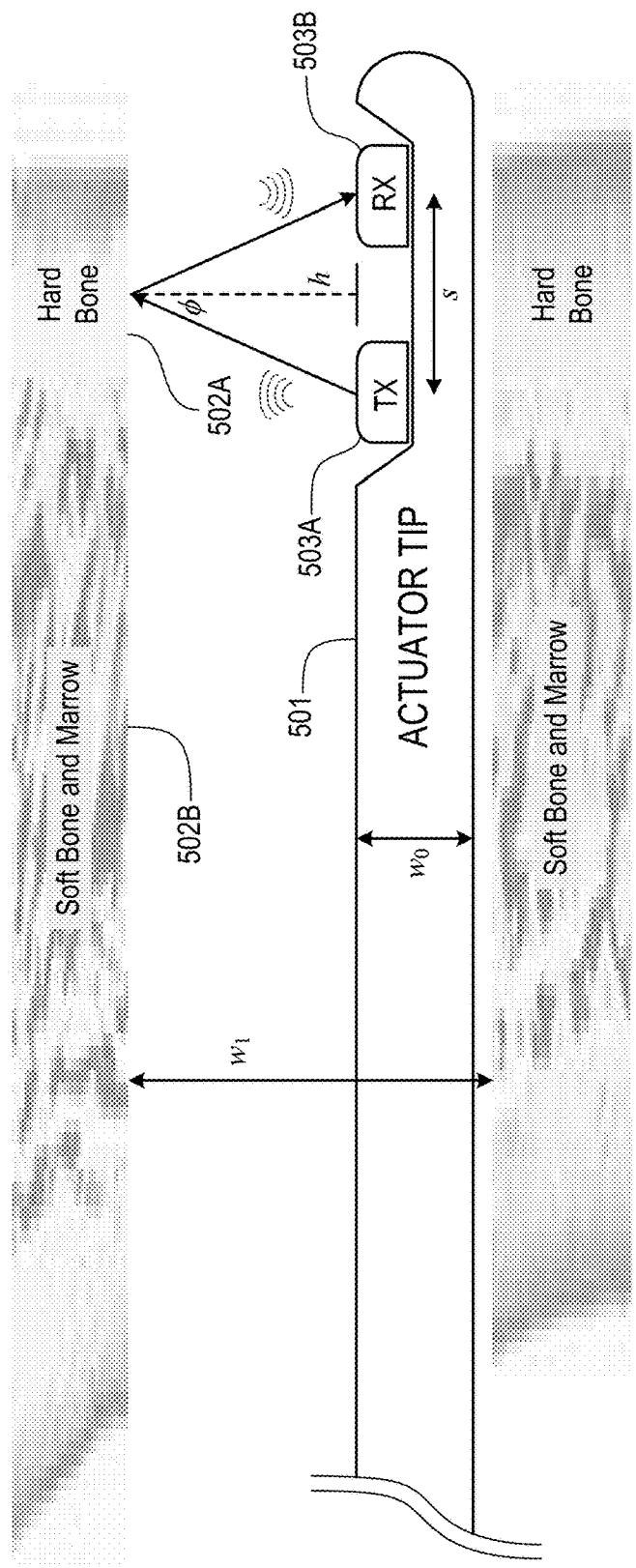
FIG. 6A illustrates a portion of an apparatus according to the present invention, in use, detecting a boundary between soft tissue and hard bone, which according to a representative embodiment of the present invention, utilizes a linear actuator with a tip having a first transducer for transmitting an ultrasonic wave toward the surface of a drilled bone and a second transducer for receiving a reflected ultrasonic wave from the same surface of the drilled bone, both disposed at the surface of the linear actuator.

In the preferred embodiments of the invention, the tip of a linear actuator (e.g., actuator 245 of assembly 200) is aligned with the distal end of a drilled bone using the transmission and reception of ultrasonic waves. This process is illustrated first with the aid of FIG. 6A, which depicts an exemplary actuator tip (e.g., actuator tip 501) that includes an ultrasonic (position) sensor with a first transducer (e.g., transmitting element 503A) for transmitting ultrasonic waves toward hard bone surface 502A, and a second transducer (e.g., receiving element 503B) for receiving ultrasonic echo that is reflected from hard bone surface 502A. For illustrative purposes, the width $w_0$ of actuator tip 501 is shown to be significantly smaller than the width $w_1$ of the drilled hole. But in practice, the width of the actuator tip can be approximately equal to the width of the drilled hole. At the hard bone surface, the intensity of the reflected echo $I_r$) is given by the equation $$I_r/I_0=(Z_2-Z_1)^2/(Z_2+Z_1)^2,$$

where $I_0$ is the incident intensity of the transmitted ultrasonic wave, $Z_2$ is the acoustic impedance of hard bone surface 502A, and $Z_1$ is the acoustic impedance of the watery material/gel that fills the drilled hole. The acoustic impedance of a material is the product of the density of that material and the velocity of sound through that material. Table 1 provides the density, velocity of sound, and acoustic impedance for various materials found commonly within the human body.

TABLE 1

Acoustic Properties of Materials

| Material | Density (kgm$^{-3}$) | Velocity (ms$^{-1}$) | Impedance (kgm$^{-2}$s$^{-1}$) |
| --- | --- | --- | --- |
| Air | 1.3 | 330 | 0.429 |
| Water | 1000 | 1450 | 1.50 × 10$^6$ |
| Bone | 1500 | 4000 | 6.00 × 10$^6$ |
| Blood | 1060 | 1570 | 1.59 × 10$^6$ |
| Muscle | 1075 | 1590 | 1.70 × 10$^6$ |
| Soft Tissue | 1050 | 1500 | 1.58 × 10$^6$ |
| Fat | 925 | 1450 | 1.38 × 10$^6$ |

According to the values in Table 1, the intensity of the ultrasonic echo that is reflected from hard bone (i.e., Z=6.00×10$^6$) is more than 500 times higher (>27 dB) than the intensity of the ultrasonic echo that is reflected from soft tissue (i.e., Z=1.58×10$^6$), assuming that the drilled hole is filled with a watery material/gel (i.e., Z=1.50×10$^6$). In addition to reflected echo, the signal arriving at receiving element 503B includes undesired crosstalk from transmitting element 503A. The intensity $I_x$ of this undesired crosstalk depends on the separation s between the transmitting and receiving elements. Conventional ultrasonic transducers (see Zhou, et. al., "Reducing Inter-Element Acoustic Crosstalk in Capacitive Micromachined Ultrasound Transducers", IEEE Transactions on Ultrasonics, Ferroelectrics, and Frequency Control, 2007) have been demonstrated that exhibit better than 30 dB crosstalk isolation at a separation of s=0.158 mm (i.e., the intensity of crosstalk into receiving element 503B is 30 dB lower than the intensity of the ultrasonic transmission from transmitting element 503A at a distance of 0.158 mm, such that $I_x/I_0$=−30 dB). The separation s between the transmitting and receiving elements (e.g., transducers 503A&B), also determines the angle φ at which ultrasonic waves are reflected from hard bone surface 502A, according to the equation $$\phi=\tan^{-1}(s/(2 \cdot h)),$$

where h equals the vertical distance between transducers 503A&B and hard bone surface 502A. A separation of s=0.158 mm and a height h=1 mm result in a reflection angle of φ=4.5°. Conventional ultrasonic transducers are relatively narrow beamwidth devices, with typical 3 dB beamwidths of ±5°, meaning that transmitted and received ultrasonic waves are subjected to a pointing loss (attenuation) of >3 dB at reflection angles of φ>5°. For reliable detection of reflected echo, therefore, the beamwidth of the transmitting and receiving elements (e.g., transducers 503A&B) preferably is larger than the expected angle of refection φ and more preferably, the separation s between the transmitting and receiving elements is such that the intensity of the signal arriving at the receiving element is measurably larger than the intensity of coupled crosstalk, after accounting for any pointing losses related to the transducer beamwidth relative to the expected reflection angle φ.

In the preferred embodiments, a physical boundary between hard bone and softer tissue is detected by monitoring levels of reflected echo (e.g., the intensity level of reflected echo preferably is converted to a monitor signal with a magnitude that is proportional, or at least approximately proportional, to the intensity). Based on typical acoustic impedances (e.g., the values shown in Table 1), the level of reflected echo when the ultrasonic sensor (e.g., transducers 503A&B in FIG. 6A) at the actuator tip is located beneath hard bone, is more than 500 times (>27 dB) higher than the level of reflected echo when the ultrasonic sensor is located beneath softer tissues, such as bone marrow or blood. Furthermore, the level (intensity) of reflected echo when the ultrasonic sensor at the actuator tip is located beneath hard bone is ~100 times (~20 dB) higher than typical crosstalk levels based on: 1) an isolation of 30 dB (i.e., $I_x/I_0$=−30 dB); 2) a round-trip pointing loss of 6 dB (i.e., 3 dB pointing loss in each of an incident and a reflected direction); and 3) a reflected intensity $I_r$ given by $$I_r/I_0=(Z_2-Z_1)^2/(Z_2+Z_1)^2,$$

for $Z_2$=6.00×10$^6$ (i.e., the acoustic impedance of hard bone from Table 1) and $Z_1$=1.50×10$^6$ (i.e., the acoustic impedance of watery material/gel from Table 1). In the preferred embodiments, the separation s between the transmitting and receiving elements is such that the intensity of the signal arriving at the receiving element is larger than the intensity of coupled crosstalk by at least a factor of 2 (3 dB), after accounting for the pointing losses from a non-zero angle of reflection φ. Detection of the boundary between hard bone and softer tissue, therefore, preferably involves the identification of relatively large differences (e.g., differences of a factor of 2 to 100) between measured intensities of reflected echo which occur as the ultrasonic sensor at the actuator tip (e.g., the tip of linear actuator 245 of assembly 200) passes through the drilled hole, and moves from regions where the ultrasonic sensor is aligned with hard bone to regions where the ultrasonic sensor is aligned with softer tissues (e.g., transducers 503A&B of FIG. 6A move from locations beneath hard bone to locations beneath softer tissues).

In embodiments where the desired separation s between the transmitting and receiving elements of the ultrasonic sensor produces significant and unacceptable levels of crosstalk (e.g., a level of crosstalk that is less than a factor of 2 smaller than the received level of reflected echo), the transmitting element can be pulsed on and off, such that due to the propagation delay of the reflected ultrasonic wave, there is a period of time at the end of the transmitted pulse where the reflected echo is present and the crosstalk is absent. It would be during this period of time that the reflected echo, and the associated boundary between hard bone and softer tissue, is preferably detected. For example, for a vertical distance between transducers 503A&B and hard bone surface 502A of h=1 mm, and an effective (theoretical) separation between transmitting element 503A and receiving element 503B of s=0 mm, the resulting angle of reflection is $\phi=0°$ and the round-trip distance d traversed by the incident and reflected ultrasonic wave is d=2·h=2 mm. According to the velocity of sound in a watery medium (e.g., the assumed material between ultrasonic transducers 503A&B and hard bone surface 502A), this round-trip distance equates to a round-trip delay of $\tau=d/v_{water}=(2\times10^{-3}$ m$)/(1450$ ms$^{-1})$ =1.38 μs. In such a representative embodiment, therefore, the detection of reflected echo takes place during a 1.38 μs period that occurs after the pulsed interval of ultrasonic transmission.

Figure 6B:
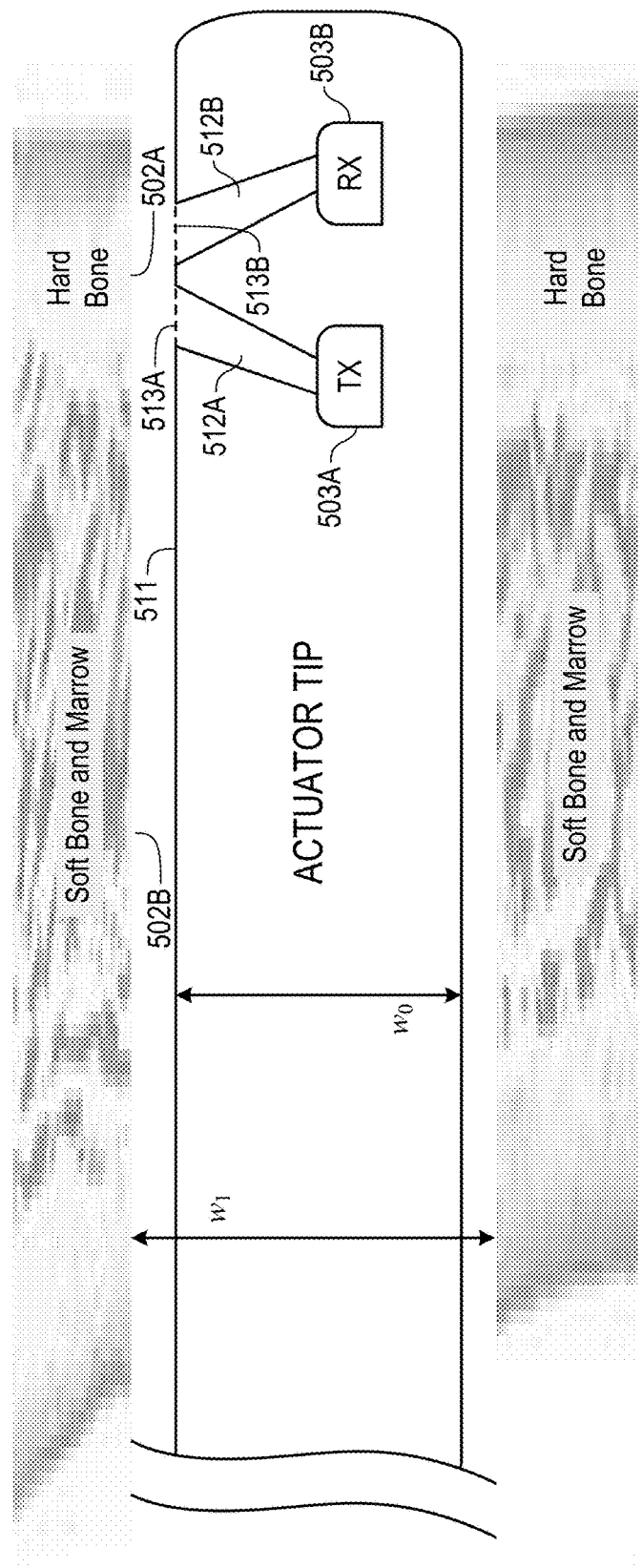
FIG. 6B illustrates an alternate embodiment with the sensor (transmitter and receiver) embedded within the interior of the tip of the actuator.

As indicated above, the sensor comprising transducers 503A&B is mounted near the surface of actuator tip 501, and the diameter (or, more generally, width) of actuator tip 501 sometimes will be approximately equal to the diameter or width of the drilled hole. Certain parameters, however, depend upon the distance between the sensor (transmitter 503A and receiver 503B) and the inner surface of the drilled hole. Accordingly, in an alternate embodiment, shown in FIG. 6B, the sensor (which includes transducers 503A&B in the current embodiment) is embedded within the interior of the actuator tip 511, rather than being mounted to the surface of the actuator tip. In such an embodiment, a first channel (e.g., channel 512A) leads from transmitting element 503A to the rest of the surface of actuator tip 511, and a second channel (e.g., channel 512B) leads from the rest of the surface of actuator tip 511 to receiving element 503B. Such a structure typically can ensure a minimum distance (height) from the sensor to the inner surface of the drilled hole, thereby reducing the angle of reflection $\phi$ and the associated pointing loss. In addition, particularly when using a material for the actuator tip 511 having a high (or at least significant or substantial) degree of acoustic insulation (or, more generally, insulation relative to the type and frequency of transmission being used), the use of channels 512A&B in conjunction with the rest of the structure of actuator tip 511 often can increase the directionality of the sensor and/or reduce crosstalk between transmitting element 503A and receiving element 503B. Finally, the use of such a structure often can help protect the sensor and increase the overall smoothness of the surface of actuator tip 511, thereby facilitating its insertion within the drill hole. Preferably, when used, each of channels 512A&B has a length of at least 1.0 to 2.0 millimeters (mm) and, more preferably, at least 3 mm.

According to one implementation, actuator tip 511 is solid (other than sensor elements 503A&B and channels 512A&B) and made of a made of a material that has a high level of impedance to the type of transmissions being used. For example, the structure may be injection molded around sensor elements 503A&B and the cables (not shown) attaching them to the rest of the apparatus's circuitry. Openings 513A&B may be left uncovered or, e.g., in order to further protect sensor elements 503A&B and provide a more uniform surface for actuator tip 511, may be covered by windows (e.g., made of a material that is highly transmissive of the type of transmissions being used. Also, as noted above, in alternate embodiments sensor elements 503A&B are replaced with a single transceiver element, and a single channel is used in place of channels 512A&B.

Figure 7A:
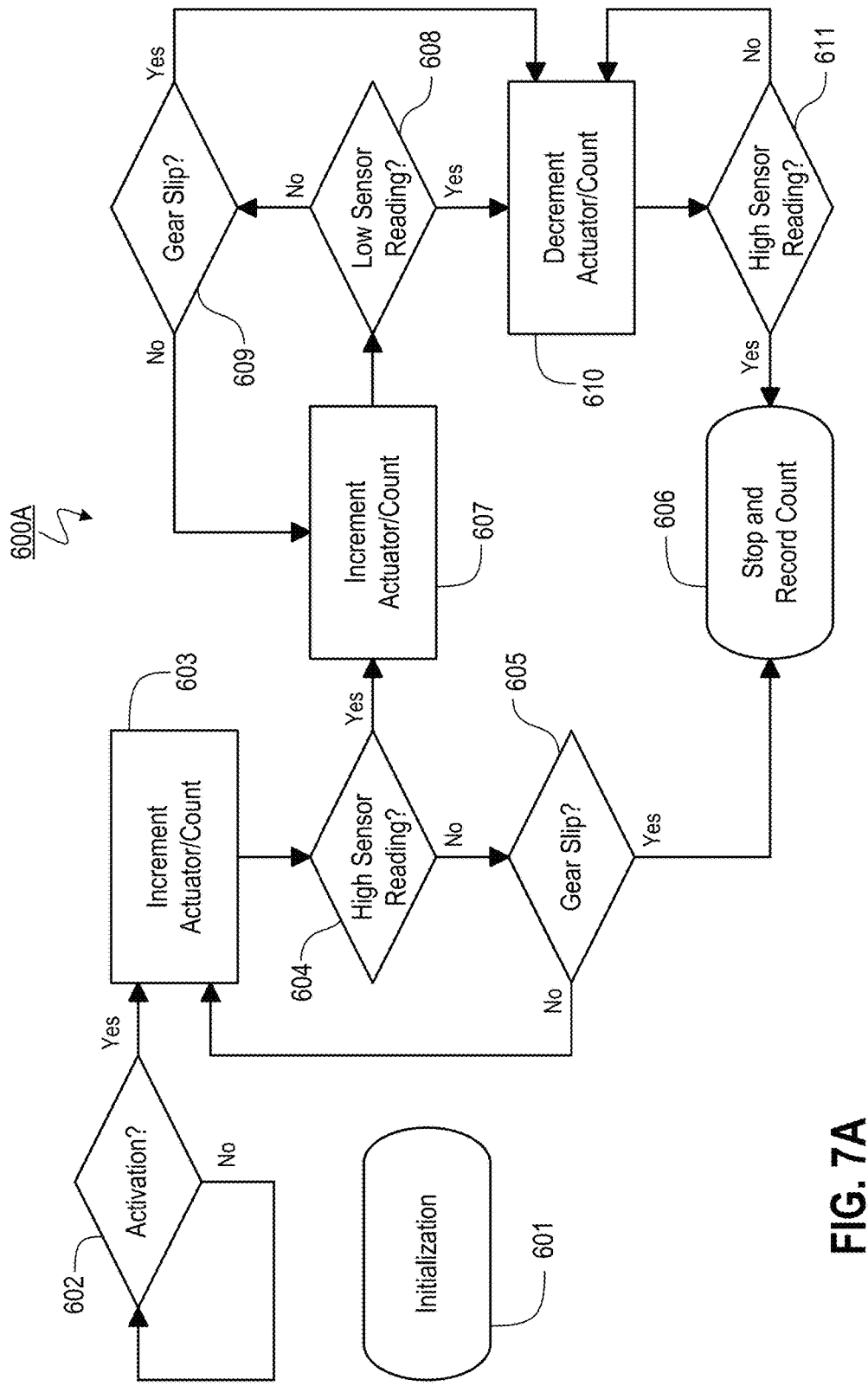
FIG. 7A is a flow diagram illustrating the processing steps associated with an autonomous bone-depth measurement according to a representative embodiment of the present invention where sensor alignment is accomplished using a motor-driven mechanism.

In the preferred embodiments, the stepper mechanism (e.g., stepper encoder 125 of assembly 100, and stepper motor 225 of assembly 200) is controlled by a machine-implemented process that involves little or no user intervention other than the activation of the process (e.g., an automated algorithm is executed by controller module 115 of assembly 100 or microprocessor 215 of assembly 200). A flow diagram for an exemplary process 600A that can provide for semi-autonomous or autonomous measurements of bone-hole depth, when coupled with an assembly according to the preferred embodiments of the present invention (e.g., assembly 100 or 200), is given in FIG. 7A. Once activated in step 602 (e.g., via a tactile command to switch module 105 or 205 of assembly 100 or 200, respectively), process 600 iteratively locates the distal end of a drilled-bone boundary, based on feedback from a sensor module (e.g., transitions in the magnitude of the output signal from position sensor 155 of assembly 100, e.g., ultrasonic sensor 255 of assembly 200). Prior to activation in step 602, an initialization step 601 brings the location of the sensor module to a position (i.e., a reset position) which is known relative to the edge of the handle making contact with the proximal bone surface, and which is clear of the proximal boundary of a drilled bone. The location of the sensor module can be reset at the time of manufacture, or can be reset just prior to activation 602, during a surgical procedure using a limit switch, for example, to bring the sensor module into a fully receded position within the handle (main housing). The sensor module can be made clear of the proximal boundary of the drilled bone by various procedures, including: 1) manually extending the shaft of the linear actuator (e.g., linear actuator 145 & 245) to a desired location; and 2) using a software subroutine that extends the shaft of the linear actuator until sensor readings make a high-to-low transition through a desired threshold (e.g., until sensor readings indicate the crossing a proximal boundary between hard bone and softer tissue).

With both the position of the sensor module properly initialized (e.g., either manually or automatically at step 601), and the confirmation of an activation command in step 602, the stepper function (e.g., stepper/encoder 125 of assembly 100 or stepper motor 225 of assembly 200) is incremented in step 603 to effect a small controlled forward movement of linear actuator 145 or 245 relative to the handle 151. Also in step 603, a count is maintained of the total net number of incremental forward movements made by the actuator during the entirety of process 600A (i.e., following initialization 601 and activation 602). After each of the controlled forward movements effected in step 603, a sensor reading is examined in step 604 to determine if the measured intensity of the reflected echo remains at a baseline level, or has undergone a transition to higher value (e.g., a value from the receiving elements of sensors 155 or 255 which preferably is a factor of 2 or more greater than a baseline value). A baseline value for the intensity of reflected echo preferably is established from multiple sensor readings made during the early incremental movements of actuator 145 or 245 (e.g., an average of sensor readings made during the beginning increments when the senor is aligned with soft tissue in the interior of the drilled hole), but in alternate embodiments, the baseline intensity level can be based on a single sensor reading or on a moving average taken over multiple sensor readings. Assuming that a gear slip is not detected at step 605, incremental movements of the actuator continue in step 603 until a low (baseline) to high transition in sensor readings is detected in step 604, at which point the incrementing of the stepper function continues in step 607, until the measured intensity of reflected echo is determined in step 608 to have undergone a transition from a high value to a low (baseline) value, or a gear slip is detected in step 609 (e.g., a gear slip occurring when the probe tip encounters the resistance of muscle and skin lining the outer part of the bone). If a high to low (baseline) transition in sensor readings is detected in step 608 or a gear slip is detected in step 609, the stepper function is decremented in step 610 (resulting in a small fixed amount of retraction of the linear actuator (145 or 245), until in step 611, high intensity readings from the sensor are reestablished. At this point in process 600A, the measurement routine terminates at step 606, and the final count is recorded of the total net number of incremental movements (i.e., the sum of the positive and negative increments) taken by the linear actuator (145 or 245). The measurement routine also terminates at step 606, if at step 605, a gear slip is detected which indicates an obstruction is preventing any further advancement of the actuator through the drilled hole (e.g., an obstruction caused by the bone surface at the distal end of a blind hole).

In the preferred embodiments, a final length of the hole also is calculated in step 606 and displayed (e.g., on display unit 135, 135B or 235). As noted previously, this calculation preferably involves multiplying the final net step count by the step distance increment and adding or subtracting a constant. In most embodiments, the constant preferably will depend upon the manner in which the process terminated, i.e., a gear slip which indicates a partially drilled hole or a high-to-low transition in sensor reading which indicates the distal end of a through hole. In the former case, the total distance typically will extend to the very tip of the linear actuator (which encounters the distal end of the partially drilled hole), while in the latter case the distance will extend to a (typically shorter) point corresponding to the sensor (e.g., a point between sensor elements 503A&B) and, therefore, a larger constant typically will be added in the former case as compared to the latter. The constant will also account for the distance from the edge of the handle making contact with the proximal bone surface (e.g., the edge of main housing 151 from which actuator 145B extends), to the tip of the linear actuator in the case of a blind hole, or to the point corresponding to the sensor in the case of through hole, when the linear actuator is in the reset position established during initialization step 601.

Summarizing, the process 600A effectively increments the stepper function until one of two conditions occur: 1) the sensor at the actuator tip reaches the distal surface of a partially drilled bone, as indicated by a gear-slip signal at step 605; or 2) the sensor at the actuator tip is aligned with the distal boundary of a drilled bone, as indicated by higher than baseline readings of reflected (or echoed) levels at step 611. When the sensor reaches the distal surface of a partially drilled bone (i.e., the sensor reaches the end of a blind hole), or the sensor is aligned with distal boundary between hard bone and softer tissue, the measurement terminates and a result is displayed (e.g., when step 606 is reached, a measure of the depth of the drilled hole is displayed on display unit 135 of assembly 100 or digital display 235 of assembly 200). The result is a measure of the depth of the drilled hole, which preferably is calculated based on the total number of incremental forward movements made the actuator times the distance traversed with each incremental forward movement (i.e., the total number of forward movements is equal to the number of incremental movements minus the number of decremental movements). It should be noted that for the case of a completely drilled hole, the accuracy of the bone-depth measurement is improved in certain embodiments by repeatedly incrementing and decrementing the stepper function near the distal boundary of the hole, so that before the measurement terminates and the result is displayed, the sensor is located at a position corresponding to a peak in the measured intensity of reflected echo (e.g., steps 607 to 611 of process 600A are repeated using feedback from the sensor for more accurate alignment).

Figure 7B:
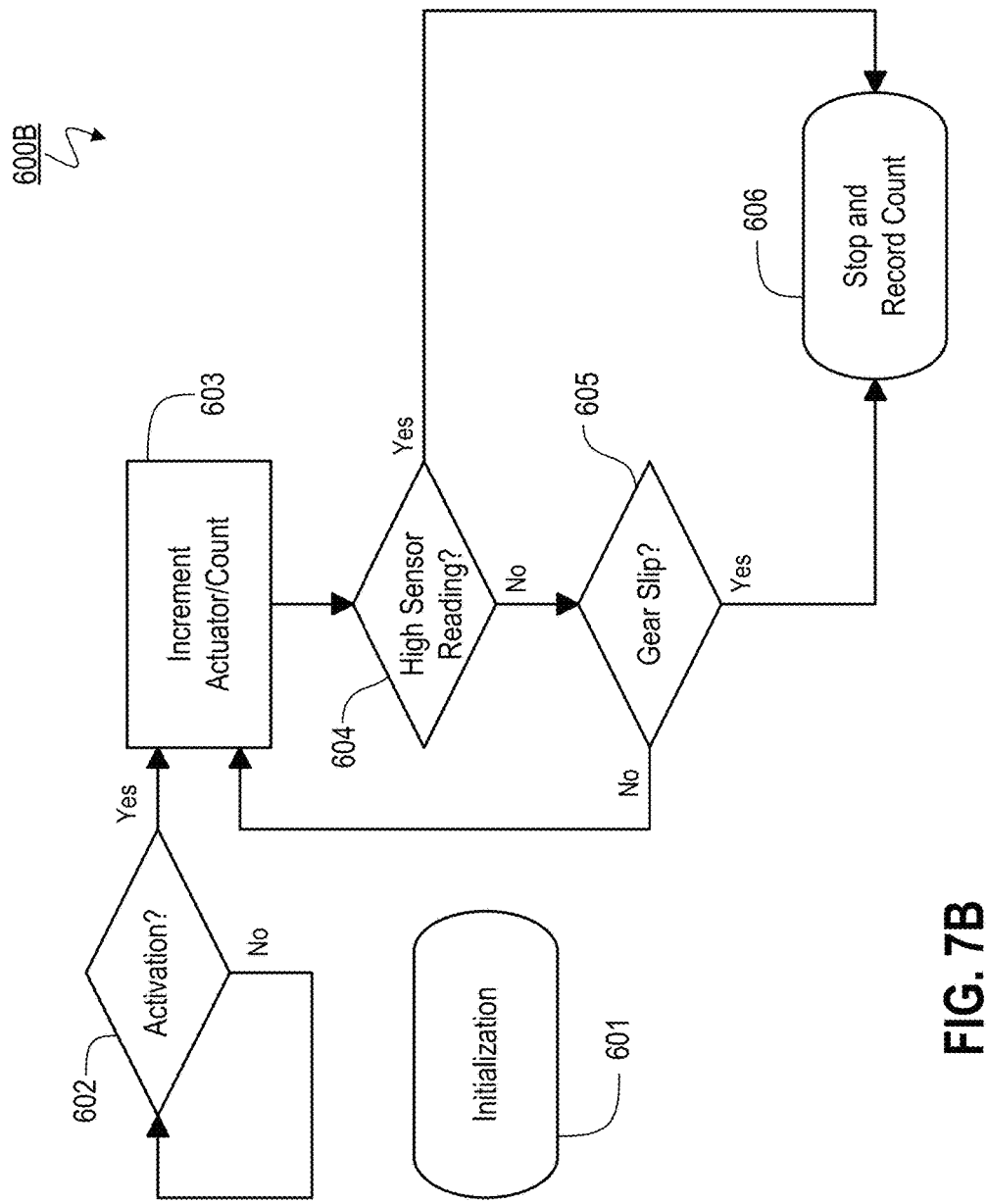
FIG. 7B is a flow diagram illustrating the processing steps associated with a bone-depth measurement according to a representative embodiment of the present invention where sensor alignment is accomplished using a hand-driven mechanism.

Also, in certain embodiments where the position of the actuator is incremented by a hand-driven ratcheting mechanism, an abbreviated measurement process is utilized in which the actuator moves only in a forward direction. However, in alternate such embodiments, the operator has the ability to increment (extend the linear actuator 145) or decrement (retract the linear actuator 145) in a fixed amount as desired. Such an exemplary abbreviated measurement routine is process 600B, illustrated in FIG. 7B, which includes only steps 601 to 606 of exemplary process 600A. In this embodiment, most of the steps are performed by the human operator, e.g., manually advancing (and, in some implementations, retracting) the linear actuator 145 in step 603, looking for sensor reading transitions in step 604 (with an indication of the sensor readings preferably also displayed), and looking for a gear slip condition in step 605 (i.e., a failure of the displayed length measurement to increase, despite an attempted increment in step 603).

In certain embodiments of the invention, rather than (or in addition to) including a display unit (135, 135B or 235) on the apparatus, the apparatus includes a wireless transmitter that transmits the display information (e.g., using Bluetooth, near-field communications and/or Wi-Fi protocols) to an external device for display. Such a feature can be particularly important when performing the manual process 600B, where it might be otherwise difficult for the operator to conveniently view an onboard display unit while the apparatus is being used.

Additional Considerations

Several different embodiments of the present invention are described above, with each such embodiment described as including certain features. However, it is intended that the features described in connection with the discussion of any single embodiment are not limited to that embodiment but may be included and/or arranged in various combinations in any of the other embodiments as well, as will be understood by those skilled in the art.

As used herein, the term "coupled", or any other form of the word, is intended to mean a mechanical connection or an electronic connection, which is either made directly or made through one or more other processing blocks, e.g., for the purpose of preprocessing or forming linkages.

In the preceding discussion, the terms "operators", "operations", "functions" and similar terms can refer to method steps or hardware components, depending upon the particular implementation/embodiment.

Words such as "optimal", "optimize", "minimize", "maximize", "best" and similar words are used throughout the above discussion. However, it should be understood that, except to the extent clearly indicated to the contrary, such words are not used in their absolute sense, but rather are intended to be viewed in light of other constraints, such as user-specified constraints and objectives, as well as cost and processing constraints.

In the above discussion, certain methods are explained by breaking them down into steps listed in a particular order. However, it should be noted that in each such case, except to the extent clearly indicated to the contrary or mandated by practical considerations (such as where the results from one step are necessary to perform another), the indicated order is not critical but, instead, that the described steps can be reordered and/or two or more of such steps can be performed concurrently.

References herein to a "criterion", "multiple criteria", "condition", "conditions" or similar words which are intended to trigger, limit, filter or otherwise affect processing steps, other actions, the subjects of processing steps or actions, or any other activity or data, are intended to mean "one or more", irrespective of whether the singular or the plural form has been used. For instance, any criterion or condition can include any combination (e.g., Boolean combination) of actions, events and/or occurrences (i.e., a multi-part criterion or condition).

In the discussions above, the words "include", "includes", "including", and all other forms of the word should not be understood as limiting, but rather any specific items following such words should be understood as being merely exemplary.

Similarly, in the discussion above, functionality sometimes is ascribed to a particular module or component. However, functionality generally may be redistributed as desired among any different modules or components, in some cases completely obviating the need for a particular component or module and/or requiring the addition of new components or modules. The precise distribution of functionality preferably is made according to known engineering tradeoffs, with reference to the specific embodiment of the invention, as will be understood by those skilled in the art.

Thus, although the present invention has been described in detail with regard to the exemplary embodiments thereof and accompanying drawings, it should be apparent to those skilled in the art that various adaptations and modifications of the present invention may be accomplished without departing from the intent and the scope of the invention. Accordingly, the invention is not limited to the precise embodiments shown in the drawings and described above. Rather, it is intended that all such variations not departing from the intent of the invention be considered as within the scope thereof as limited solely by the claims appended hereto.

What is claimed is:

1. An apparatus for performing a measurement of the depth of a drilled hole, comprising:
    a controller module having a first and second input, and also having a first and second output;
    a switch module having an output coupled to the first input of said controller module, and which provides a command interface to a human operator through a tactile element;
    a stepper/encoder unit having an input coupled to the first output of said controller module, and also having an output;
    a linear actuator driven by said stepper/encoder unit, and also having a segment which can be inserted into said drilled hole;
    a position sensor mechanically coupled to said linear actuator, and also having an output; and
    a display unit which is coupled to the second output of said controller module, and which provides a readout to a human operator,
    wherein said controller module controls said stepper/encoder unit and, based on input from said position sensor, executes an algorithm for (i) at least one of semi-autonomous or fully autonomous alignment of said distal end of said linear actuator with a distal end of said drilled hole and (ii) calculating linear displacement of said linear actuator,
    wherein said stepper/encoder unit converts commands from said controller module into discrete amounts of at least one of angular or linear mechanical movement,
    wherein said linear actuator slides back and forth in response to the angular or mechanical movements of said stepper/encoder unit,
    wherein said position sensor produces an electronic signal having a magnitude transition indicating when the end of said drilled hole has been reached, and
    wherein the display unit provides a readout indicating a measure of the linear displacement of said linear actuator.

2. An apparatus according to claim 1, wherein said controller module calculates said measurement of linear displacement based on a product of a constant and a total number of steps executed by said stepper/encoder unit.

3. An apparatus according to claim 1, wherein said stepper/encoder unit includes a stepper motor.

4. An apparatus according to claim 1, wherein said stepper/encoder unit includes at least one of a linear motor or an angular position sensor.

5. An apparatus according to claim 1, further comprising a slip gear mechanism that detects when a physical impediment causes a command to said stepper/encoder unit to produce no incremental displacement of said linear actuator.

6. An apparatus according to claim 1, wherein said position sensor includes at least one of a sonic or an ultrasonic transmitter.

7. An apparatus according to claim 6, wherein said position sensor includes a capacitive micromachined ultrasonic transducer.

8. An apparatus according to claim 6, wherein said position sensor includes a piezoelectric micromachined ultrasonic transducer.

9. An apparatus according to claim 1, wherein said position sensor includes a radio-frequency (RF) transmitter.

10. An apparatus according to claim 1, wherein said position sensor includes an optical transmitter.

11. An apparatus according to claim 1, wherein said stepper/encoder unit is coupled to said linear actuator via a gear mechanism that converts angular motion to linear motion.

12. An apparatus according to claim 1, wherein said position sensor is coupled said controller module via an analog-to-digital converter.

13. An apparatus according to claim 1, wherein said controller module is implemented using a microprocessor.

14. An apparatus according to claim 1, wherein said controller module, switch module, stepper/encoder unit, linear actuator, position sensor and display unit are disposed within a housing which can be held in a single hand and, while doing so, said switch module can be operated by said single hand.

* * * * *